(12) United States Patent
Kern

(10) Patent No.: US 8,820,317 B2
(45) Date of Patent: Sep. 2, 2014

(54) TURBO-INHALER

(75) Inventor: Joachim Kern, Elsenfeld (DE)

(73) Assignee: Unither Therapeutik GmbH, Elsenfeld (DE)

( * ) Notice: Subject to any disclaimer, the term of this patent is extended or adjusted under 35 U.S.C. 154(b) by 299 days.

(21) Appl. No.: 13/380,580

(22) PCT Filed: Jun. 23, 2010

(86) PCT No.: PCT/DE2010/000715
§ 371 (c)(1),
(2), (4) Date: Mar. 20, 2012

(87) PCT Pub. No.: WO2010/149144
PCT Pub. Date: Dec. 29, 2010

(65) Prior Publication Data
US 2012/0174916 A1  Jul. 12, 2012

(30) Foreign Application Priority Data

Jun. 24, 2009  (DE) .................. 10 2009 030 185

(51) Int. Cl.
*A61M 11/00* (2006.01)
*B01D 45/16* (2006.01)
*B01D 45/08* (2006.01)
*A61M 15/00* (2006.01)

(52) U.S. Cl.
CPC ........... *A61M 15/0085* (2013.01); *B01D 45/16* (2013.01); *B01D 45/08* (2013.01); *A61M 2206/14* (2013.01); *A61M 11/005* (2013.01); *A61M 11/002* (2013.01)
USPC ............ 128/200.21; 128/200.16; 128/200.17; 128/200.18; 239/338

(58) Field of Classification Search
CPC . A61M 11/02; A61M 15/00; A61M 15/0086; A61M 11/00
USPC ............ 128/200.14, 200.16, 200.17, 200.18, 128/200.21; 239/338
See application file for complete search history.

(56) References Cited

U.S. PATENT DOCUMENTS 3,795,244 A *  3/1974  Lax et al. ................. 128/203.15
3,885,934 A    5/1975  Eads et al. .................... 55/457

(Continued)

FOREIGN PATENT DOCUMENTS

CA    2207219        12/1998
DE    10 2006 026 786 A1    12/2007

(Continued)

OTHER PUBLICATIONS

International Search Report of PCT/DE2010/000715, dated Sep. 29, 2010, 6 pgs. (with English translation).
International Preliminary Report on Patentability for PCT Application No. PCT/DE2010/000715, dated Jan. 17, 2012, 2 pages.

(Continued)

*Primary Examiner* — Steven Douglas
(74) *Attorney, Agent, or Firm* — Foley & Lardner LLP

(57) ABSTRACT

The invention relates to a turbo-inhaler, comprising an active-liquid container (1) holding a liquid having an active ingredient dissolved therein, a nebulizer (2), by means of which liquid can be converted into an aerosol and introduced into a blade housing (3), in which a bounding dome (4) is suspended, the concave side (41) of which is directed at the nebulizer, an exhaust air duct (5), which is connected to the blade housing in the area of the convex side (42) of the bounding dome, and a supply-air guide (6), by means of which supply air can be introduced between the blade housing and the active ingredient, wherein at least one guide blade (7) is placed on the convex side of the bounding dome and spirally extends thereon.

8 Claims, 1 Drawing Sheet

(56) References Cited

U.S. PATENT DOCUMENTS

| | | | |
|---|---|---|---|
| 4,429,835 A * | 2/1984 | Brugger et al. | 239/338 |
| 5,054,477 A * | 10/1991 | Terada et al. | 128/200.14 |
| 5,503,139 A * | 4/1996 | McMahon et al. | 128/200.18 |
| RE36,070 E * | 2/1999 | Ballini et al. | 128/200.14 |
| 5,875,774 A * | 3/1999 | Clementi et al. | 128/200.18 |
| 5,881,715 A | 3/1999 | Shibasaki | 128/200.14 |
| 6,482,245 B2 * | 11/2002 | Brilmaker | 55/394 |

FOREIGN PATENT DOCUMENTS

| | | |
|---|---|---|
| EP | 0 504 459 A1 | 3/1991 |
| GB | 2 224 446 | 5/1990 |
| JP | 63-077460 A | 4/1993 |

OTHER PUBLICATIONS

Written Opinion for International Search Report dated Sep. 29, 2010 for PCT Application No. PCT/DE2010/00715, 5 pages.

* cited by examiner

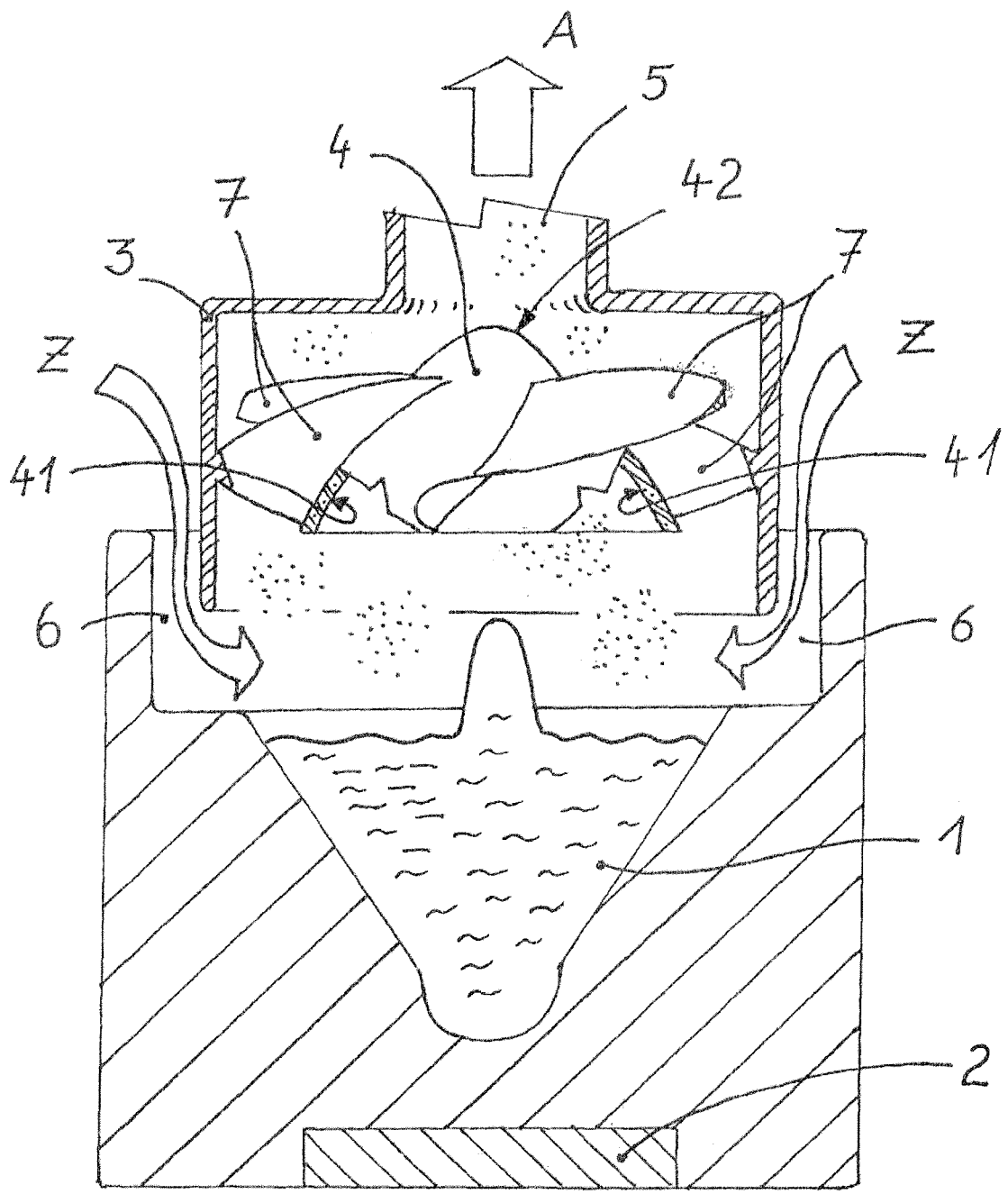

TURBO-INHALER

CROSS-REFERENCE TO RELATED APPLICATION

This Application is a Section 371 National Stage Application of International Application No. PCT/ DE2010/000715, filed Jun. 23, 2010 and published as WO 2010/149144 on Dec. 29, 2010, in English, the contents of which are hereby incorporated by reference in their entirety.

The invention relates to a turbo inhaler, consisting of an active liquid container, which contains a liquid having an active substance dissolved therein, and a nebulizer, by means of which the liquid can be transformed into an aerosol and introduced into a vane housing, in which a bounding dome is suspended, of which the concave side faces the nebulizer, and an exhaust air tube, which, in the region of the convex side of the bounding dome is connected to the vane housing, and a supply air guide, by means of which the supply air can be introduced between the vane housing and the active substance container.

In the prior art, inhalers have become a well proven method for conveying a medicament and other active substances in liquid form, together with the respiratory air, into the lungs of humans and animals, from where they are very rapidly transferred to the blood stream with low loss.

The mechanical atomizers of the prior art, which force the liquid through a nozzle to convert it into an aerosol, that is to say to form a mist, are currently very frequently replaced by usually conical active substance containers, below which a piezo crystal is disposed as nebulizer, which generates an ultrasonic oscillation and transfers it to the active liquid. As a result, a spray forms on the liquid surface, which separates out the active liquid as an aerosol, that is to say a mixture of air and extremely find droplets of the active liquid. The aim is to generate drops that are as small as possible, the diameter of which should not exceed four micrometres, and for which the greatest possible proportion of the droplets has a diameter close to two micrometres.

In the prior art, German patent DE 19838711 discloses a bounding dome above the spray, which turns its concave side towards the spray. This bounding dome catches splashes from the active substance container that are formed in particular when the liquid level is dropping, and guides these amounts of liquid back into the active container.

In the dome-shaped depression of the bounding dome, aerosols emerging from the spray are also forced in, slide along the inner surface and, on leaving the dome, very quickly change their direction, that is to say execute an approximately 180 degree turn, and then flow through the gap between the bounding dome and the housing, in which said dome is fastened. Due to this rapid change of direction, the biggest droplets of the aerosol are accelerated against the wall of the housing, where they remain adhered and agglomerate into droplets, which fall back into the active substance container. The small droplets of the aerosol, on the other hand, are entrained by the respiratory air and sucked out of the exhaust air tube, above the bounding dome.

As a further refinement of this principle, German patent DE 101 01 454 discloses additional baffle plates, which are disposed, transverse to the flow, in the interspace between the bounding dome and the housing, and force the aerosol into the gap between the baffle plate and bounding dome. These additional baffle surfaces ensure a further reduction of the proportion of droplets with a relatively small diameter, a diameter of 5 micrometres and more being classified as large.

A disadvantage of both above-described arrangements, however, is that the profile of the tubes that are contiguous with the outlet of the housing is that such a multiplicity of large aerosol droplets are entrained that fine droplets are deposited in bends of the tube or at connecting points of two tubes, combine with further drops and ultimately form liquid drops that are visible with the naked eye. In particular, if the tube is transparent, it can be seen in this way that not the entire active substance, which may be very expensive, is transported into the lung, but a portion is lost.

A further disadvantage is that these droplets in the pipe section must be carefully eliminated before further use of the inhaler to avoid mixing with the subsequent active substance of a further application.

The essential disadvantage of this principle is the very high flow resistance for the baffle plates resulting from the constrictions at the baffle plates, as a result of which the user is hindered from respiration. Since the users are often weakened by illness, that is not only uncomfortable for them but can even lead to a change of the respiration behaviour, such as shallow and irregular breathing, which in turn impairs the effectiveness of inhalation.

Against this background, it is the object of the invention to develop an inhaler that separates out aerosol droplets that are too large from the aerosol and leads them back into the active substance container, and in the process only increases the flow resistance for respiration by a very small amount.

To achieve this object, the invention teaches that at least one guide vane is mounted on the concave side of the bounding dome, and runs thereon in a spiral profile.

The crucial element of the invention is thus the guide vanes, which impart a twist to the flow, that is to say additionally give it a rotation about its longitudinal axis. As a result a centrifugal force is exerted on the aerosol droplets, which is all the greater the greater the diameter, and therefore the greater the mass of the aerosol droplet. As a result of this centrifugal force, particularly the relatively large aerosol droplets are forced against the edge of the vane housing, from where they can flow back directly into the active substance container.

In contrast to the prior art, the guide vanes are neither oriented transversely to the air stream, like the impactor walls in German patent DE 10101454, nor oriented in the direction of the air stream, as is known from the carrier of the bounding dome. Rather, the additional guide vanes are oriented obliquely to the air stream, so that the latter must change its direction. In addition, the guide vanes run in a spiral on the concave side of the bounding dome, as a result of which the direction of the air stream and the aerosol contained therein is not only changed once on encountering the guide surface, but continually, since the effective inclination of the baffle surface is continually changes due to its spiral form.

Due to this continual change of direction, a twist is imparted to the air stream. That is to say it rotates about its longitudinal axis, so that centrifugal forces act in particular on the relatively large aerosol droplets, forcing them out of the air stream onto the inner surface of the vane housing, so that they remain adhering there and agglomerate into droplets, which run along the housing wall back into the active substance container and later return as aerosol.

This effect for separating relatively large aerosol droplets can also be explained as a compressed turbulence, which forms above the dome with the mounted guide vanes.

This turbulence is homogeneous and therefore particularly efficient if a multiplicity of guide vanes are uniformly distributed around the circumference. They then act in a similar manner to a turbine, the propeller of a ship or of an aircraft, but with the substantial difference that in this case the propeller is fixed and the aerosol flows against it. After the aerosol stream leaves the guide vanes, it has a twist. It thus rotates about the longitudinal axis of its flow direction.

If this flow is reduced on entry into the exhaust air tube from the relatively large diameter of the vane housing to the relatively small diameter of the exhaust air tube, the kinetic energy of this impact movement is essentially retained. Due to the reduction of the diameter, the velocity component of the aerosol droplets tangential to the main flow direction increases significantly, as a result of which the largest droplets are deposited on the housing, where they agglomerate into larger drops, which fall through the guide vanes back into the active substance container, and are there converted into an aerosol again.

This effect also goes without saying for only a single guide vane. Such a single guide vane can, like an Archimedes screw, wind around the bounding dome. This alternative, however, has the restriction that the "return path" of the deposited aerosol droplets is very long, for which reason a larger number of guide vanes is preferred. With a growing number of guide vanes, their advantageous effect on the largest aerosol droplets also increases. This effect reaches a maximum when the entire cross-sectional area of the vane housing is covered with guide vanes in the flow direction.

Four to six guide vanes have proved in practice to be a very good number.

A further increase of the number of guide vanes only increases the flow resistance without further intensifying the deposition effect. An average pitch of the guide vanes running spirally on the bounding dome, of an order of about 45 degrees, is the preferred embodiment here. Larger or smaller average values are also possible, but are do not in general help so well to build up the twist needed to deposit the largest aerosol droplets. It should be noted that the guide vanes always run spirally around the dome and therefore only have a changing pitch when seen from only one viewpoint.

It is to be preferred that the guide vanes are uniformly distributed around the circumference of the bounding dome because the effect on the air stream is then also uniform.

The air stream resulting from the turbo inhaler according to the invention runs, in the interior thereof, along a longitudinal axis that extends from the nebulizer to the exhaust air tube. With respect to this longitudinal axis, the cross-sections of the elements of the turbo inhaler can, in the most general case, be arbitrary. However, a rotationally symmetrical construction with respect to the longitudinal axis is to be preferred. The vane housing, the bounding dome and the active substance contained then have circular cross sections and are coaxial to one another.

In a turbo inhaler according to the invention, the bounding dome can be connected to the vane housing by means of a carrier. However, it is to be preferred that at least one guide vane is so long that it extends, at least with its tip, to the vane housing and therefore, besides functioning as a guide surface for the air stream, also performs mechanical fixing of the bounding dome.

As mentioned above, it is a preferred embodiment that—seen transversely to the flow direction—the space between the vane housing and the bounding dome is completely filled with guide vanes. Then—seen in the direction of the longitudinal axis—the free edge of each guide vane, which points towards the exhaust air tube, has a clearance from the free edge of the adjacent guide vane, which points to the nebulizer. However, alternatively, it is also possible that the guide vanes overlap somewhat in the direction of the longitudinal axis, so that each guide vane projects, with its free edge, which faces the exhaust air tube, somewhat beyond the free edge of the adjacent guide vane, which points to the nebulizer.

In another embodiment, the guide vanes can be varied in their pitch by making them pivotable about a pivot axis that is transverse to the longitudinal axis. Due to an enlargement of the acute angle between the guide vanes and the longitudinal axis, the rotational velocity of the air stream is also increased. In practice, however, this embodiment will be infrequent.

Further details and features of the invention are described below with reference to an example. This is not intended to restrict the invention, but only to explain it. In schematic, view:

FIG. 1 shows a section through a turbo inhaler.

FIG. 1 shows a turbo inhaler according to the invention that is cutaway along the longitudinal axis 5-2 from the exhaust air tube 5 to the nebulizer 2. On the lowermost side thereof, there is disposed the nebulizer 2, in this case a piezo crystal, which generates ultrasound, which is transmitted to the active liquid in the active liquid container 1 that is disposed above the same. For the sake of clarity, all control elements and other functions for correct actuation of the nebulizer 2 are not shown in this section drawing. In the active liquid container 1, a spray forms in the active liquid by virtue of the excitation with ultrasound, from which fie droplets are separated as an aerosol.

Between the active liquid container 1 and the vane housing 3 disposed above the same, surrounding slits are disposed, through which supply air Z enters and mixes with the aerosol.

This aerosol enters the bounding dome 4, which is shown cut open at its two corners to show its concave side 41. The larger particles of the aerosol are accelerated onto this concave side, where they are laterally deflected and guided to the slit between the delimiting dome 4 and the vane housing 3. In FIG. 1, it can be readily understood that relatively large aerosol droplets that have collected on the concave side 41 of the bounding dome 4 agglomerate to form drops, and also splashes from the spray are reflected, which fall back into the active liquid container 1.

The remaining, finer aerosol droplets are sucked in by the exhaust air A, which is sucked out through the exhaust tube 5 during respiration, into the space between the convex side 42 of the bounding dome 4 and the inner side of the vane housing 3. There, they pass into the twist of the air stream, which is generated on the guide vanes 7, which is the decisive feature of the invention. In FIG. 1, it can be readily seen how the guide vanes 7 expand spirally on the convex side 42 of the bounding dome 41 and thereby impart a twist to the air stream.

Also in FIG. 1, it can be readily understood how the aerosols, which pass through the guide vanes 7, which are disposed in the manner of a turbine, are subjected to the twist of the air stream, the direction of rotation of which is oriented perpendicular to the longitudinal axis 5-2, and how a centrifugal force is thereby exerted on it.

If the aerosols that are set into rotation about the main flow direction are reduced from the large diameter of the inside of the vane housing 3 to the very much smaller diameter of the exhaust air tube 5, their circumferential velocity increases significantly, since their kinetic energy is substantially retained. As a result, the effective centrifugal force is increased and, at the entry point of the exhaust air tube 5, further, larger aerosol particles are deposited on the wall of the exhaust air tube 5. There, they collect with other aerosol particles and form larger drops, which then fall back into the active liquid container 1.

LIST OF REFERENCE CHARACTERS

1 Active-liquid container
2 Nebulizer 2 below the active liquid container 1, which transforms liquid into an aerosol
3 Vane housing above the active liquid container 1, takes up aerosol
4 Bounding dome, above the nebulizer 2
41 Concave side of the bounding dome 4, facing the nebulizer 2
42 Convex side of the bounding dome 4
5 Exhaust air tube, disposed opposite the convex side 42 of the bounding dome 4
5-2 Longitudinal axis from the exhaust air tube 5 to the nebulizer 2
6 Supply-air guide, guides supply air Z between the vane housing 3 and active substance container 1
7 Guide vane, mounted on the convex side 42 of the bounding dome 4
A Exhaust air, containing aerosol, exits through the exhaust-air tube 5
Z Supply air, enters through the supply air guide 6 into the space between the bounding dome 4 and the active liquid container 1.

The invention claimed is:

1. A turbo inhaler, comprising
an active substance container, which contains a liquid having an active substance dissolved therein,
a nebulizer configured to transform the liquid into an aerosol, configured to be introduced into a vane housing, in which a bounding dome is suspended, of which a concave side is directed towards the nebulizer.
an exhaust air tube connected to the vane housing in a vicinity of a convex side of the bounding dome, and
a supply air guide through which supply air is configured to be introduced between the vane housing and the active substance container, wherein at least one guide vane is mounted on the convex side of the bounding dome, and runs spirally thereon.

2. The turbo inhaler according to claim 1, wherein an interior of the vane housing, the bounding dome and the active substance container are formed so as to be symmetrical with respect to a longitudinal axis from the exhaust air tube to the nebulizer, and disposed coaxially with respect to the longitudinal axis.

3. The turbo inhaler according to claim 1, wherein a plurality of guide vanes are distributed uniformly about a circumference of the bounding dome.

4. The turbo inhaler according to claim 1, wherein at least one guide vane is connected to the vane housing and serves as a support for the bounding dome.

5. The turbo inhaler according to claim 1, wherein a free edge of each guide vane, which points towards the exhaust air tube, has, in a direction of a longitudinal axis, a clearance with respect to the free edge of an adjacent guide vane, which points towards the nebulizer.

6. The turbo inhaler according to claim 1, wherein each guide vane 7 with its free edge, which points towards the exhaust air tube, projects, in a direction of a longitudinal axis, beyond the free edge of an adjacent guide vane, which points towards the nebulizer.

7. The turbo inhaler according to claim 1, wherein a cross-section of the vane housing, transversely to a longitudinal axis, is completely covered with guide vanes individual guide vanes having a clearance from one another in a direction of a longitudinal axis.

8. The turbo inhaler according to claim 1, wherein to increase a rotational velocity of an air stream, an acute angle between the guide vanes and a longitudinal axis is configured to be increased.

* * * * *